United States Patent [19]

Honkanen et al.

[11] 4,271,300
[45] Jun. 2, 1981

[54] METHOD FOR PRODUCING 6,7-DIMETHOXY-4-AMINO-2-[4-(2-FUROYL)-1-PIPERAZINYL] QUINAZOLINE HYDROCHLORIDE HAVING AN ANTIHYPERTENSIVE EFFECT

[75] Inventors: Erkki J. Honkanen, Helsinki; Aino K. Pippuri, Espoo; Pekka J. Kairisalo, Helsinki; Heinrich Thaler, Espoo; Maija K. Koivisto, Helsinki; Sirpa A. Tuomi, Helsinki, all of Finland

[73] Assignee: Orion-yhtyma Oy, Finland

[21] Appl. No.: 110,589

[22] Filed: Jan. 9, 1980

[30] Foreign Application Priority Data

Jan. 31, 1979 [FI] Finland ................................ 790320

[51] Int. Cl.$^3$ ........................................... C07D 405/14
[52] U.S. Cl. ................................................... 544/291
[58] Field of Search ......................................... 544/291

[56] References Cited

U.S. PATENT DOCUMENTS

| 3,935,213 | 1/1976 | Hess  | 544/291 |
| 4,092,315 | 5/1978 | Bianco | 544/291 |

Primary Examiner—Paul M. Coughlan, Jr.
Attorney, Agent, or Firm—Biebel, French & Nauman

[57] ABSTRACT

An improved method is disclosed for producing antihypertensively active 6,7-dimethoxy-4-amino-2-[4-(2-furoyl)-1-piperazinyl] quinazoline hydrochloride, viz prazosine hydrochloride, by reacting methyl-N-(3,4-dimethoxy-6-cyano-phenyl)-[4-(2-furoyl)-1-piperazinyl]thioformamidate with a large excess of ammonium chloride.

4 Claims, No Drawings

METHOD FOR PRODUCING 6,7-DIMETHOXY-4-AMINO-2-[4-(2-FUROYL)-1-PIPERAZINYL] QUINAZOLINE HYDROCHLORIDE HAVING AN ANTIHYPERTENSIVE EFFECT

BACKGROUND OF THE INVENTION

1. Field of the Invention

The present invention relates to a new, improved method for producing 6,7-dimethoxy-4-amino-2-[4-(2-furoyl)-1-piperazinyl]quinazoline hydrochloride, i.e. prazosine hydrochloride, having the formula

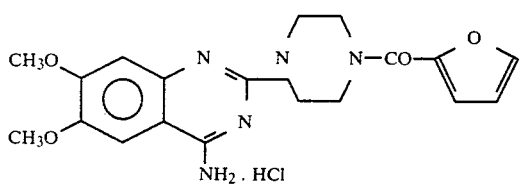

2. Description of the Prior Art

Prior methods for producing prazosine are described in the following patents, for example: U.S. Pat. No. 3,511,836, Netherlands Pat. No. 7206067, and West German Offenlegungsschrift No. 2,457,911 corresponding to U.S. Pat. No. 3,935,213.

However, there are many technical difficulties involved in carrying out the same methods in practice. Furthermore, when using these methods, the yield is rather low and the purification of the product is laborious. In the method for producing prazosine disclosed in Finnish public Patent Application No. SF-76 3614, the disadvantages appearing in the previous methods have been considerably reduced and at the same time the yield has been improved.

In the method for producing prazosine according to SF No. 76 3614, the closing of the quinazoline ring is carried out intramolecularly by using, as the initial material, methyl-N-(3,4-dimethoxy-6-cyanophenyl)-[4-(2-furoyl)-1-piperazinyl]thioformamidate, having the formula II. This compound is reacted with ammonia in formamide, in the presence of an alkaline catalyst such as sodium amide, according to the following reaction formula:

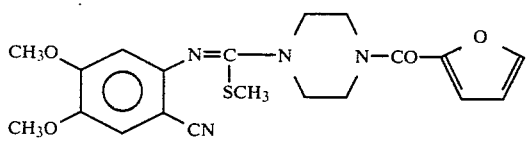

In this method, the yield of prazosine is 40–50% raw product having a purity of 95–97%. Thereafter the product must still be converted to hydrochloride, which is the actual drug, and must be crystallized a few times before the purity required of a medical drug (99.7–99.8%) is obtained. The total yield thereby decreases to about 35%.

SUMMARY OF THE INVENTION

Now it has surprisingly been observed that the yield of prazosine, and at the same time the purity of the product, can be improved considerably and the production and purification methods can be simplified, if in the above reaction closing the quinazoline ring a great excess of ammonium chloride is used, as set forth in the present invention, instead of ammonia gas. In this case, no alkaline catalyst (sodium amide, etc.) is required for carrying out the reaction. Furthermore, the desired prazosine hydrochloride is directly formed in the reaction, with a good yield (93–95%). The purity of the raw product is also very high, about 99.5%. The required degree of purity (99.7–99.8%) is obtained by a single crystallization of this raw product. The total yield is in this case 85–86%. The method for producing prazosine hydrochloride according to the invention is thus a highly notable improvement over prior methods. The practical realization of the reaction and the separation and purification of the product are substantially simplified. Furthermore, the use of sodium amide, which is difficult to handle in large amounts, is eliminated.

When ammonia and sodium amide are used, the reaction occurs in an alkaline milieu, in which case some replacement of the furoyl group, present in the prazosine molecule, by the formyl group occurs under the effect of formamide, which is used as a solvent. On the other hand, ammonium chloride solution is mildly acid and the said exchange acylation hardly occurs at all. The complete elimination of the said impurity, forming at low concentrations, has proven difficult in practice.

The methyl-N-(3,4-dimethoxy-6-cyanophenyl)-[4-(2-furoyl)-1-piperazinyl]thioformamidate (II) can be produced with a 70–75% yield by reacting 3,4-dimethoxy-6-aminobenzonitrile with methyl iodide in the manner disclosed in Finnish public Patent Application No. SF 76 3613.

DESCRIPTION OF THE PREFERRED EMBODIMENT

The following example illustrates the invention.

EXAMPLE 6,7-dimethoxy-4-amino-2-[4-(2-furoyl)-1-piperazinyl]-quinazoline hydrochloride 275 g (0.66 moles) of methyl-N-(3,4-dimethoxy-6-cyanophenyl)-[4-(2-furoyl)-1-piperazinyl]thioformamidate is dissolved in 3000 ml of formamide, and 1375 g (25.7 moles) of ammonium chloride is added while stirring. Thereafter, the reaction mixture is heated for 15–20 hours at 120° C., while stirring and also feeding nitrogen gas in order to remove the methane thiol produced (can be absorbed into a sodium hypochlorite solution). The prazosine hydrochloride produced gradually crystallizes out from the reaction mixture. After the reaction has ceased, 3–4 kg of ice is added to the mixture. The product is filtered, washed with cold water and acetone, and dried. Yield 254–259 g (93–95%). Purity 99.5% (HPLC). The product is crystallized out from about 10 liters of a mixture of water and ethanol (15:50). Yield 232–235 g (85–86%). Purity 99.7–99.8% (HPLC). The IR, NMR and mass spectra of the product are identical to the corresponding spectra of prazosine hydrochloride produced by methods previously described in the literature.

What is claimed is:

1. A method for producing 6,7-dimethoxy-4-amino-2-[4-(2-furoyl)-1-piperazinyl]quinazoline hydrochloride having an antihypertensive effect and having the formula comprising reacting methyl-N-(3,4-dimethoxy-6-cyanophenyl)-[4-(2-furoyl)-1-piperazinyl]thioformamidate having the formula

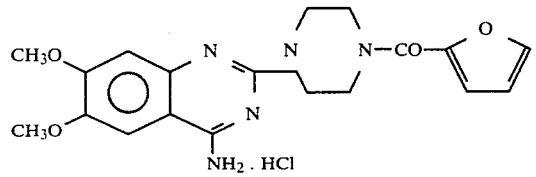

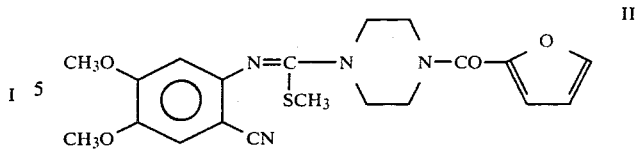

at an elevated temperature with an excess of the stoichiometric amount of ammonium chloride in a polar solvent.

2. A method as in claim 1, wherein the amount of ammonium chloride is 30–40 moles of $NH_4Cl$ per mole of the compound of Formula II.

3. A method as in claim 1, wherein the reaction is carried out in formamide at a temperature of 100°–140° C. and using a reaction period of 15–20 hours.

4. A method as in claim 3, wherein the reaction is carried out in formamide at a temperature of 120° C.

* * * * *